US00PP12768P2

(12) United States Plant Patent
Pinney, Jr.

(10) Patent No.: US PP12,768 P2
(45) Date of Patent: Jul. 9, 2002

(54) BIRCH TREE NAMED 'RENCI'

(75) Inventor: Thomas S. Pinney, Jr., Sturgeon Bay, WI (US)

(73) Assignee: Evergreen Nursery Company, Inc., Sturgeon Bay, WI (US)

( * ) Notice: Subject to any disclaimer, the term of this patent is extended or adjusted under 35 U.S.C. 154(b) by 0 days.

(21) Appl. No.: 09/395,051

(22) Filed: Sep. 13, 1999

(51) Int. Cl.[7] ..... A01H 5/00

(52) U.S. Cl. ..... Plt./216

(58) Field of Search ..... Plt./216

*Primary Examiner*—Bruce R. Campell
*Assistant Examiner*—Susan B. McCormick
(74) *Attorney, Agent, or Firm*—W. Dennis Drehkoff; Ladas & Parry

(57) ABSTRACT

A new and distinct cultivar of *Betula papyrifera* named 'Renci' characterized by its pyramidal shaped crown, rapid growth rate, only slightly exfoliating bark when mature and very high resistance to the Bronze Birch Borer.

4 Drawing Sheets

The present invention comprises a new and distinct cultivar of a birch tree, botanically known as *Betula papyrifera*, and is hereto referred to by the cultivar name "Renci".

BACKGROUND OF THE INVENTION

'Renci' was discovered by the inventor in a group *Betula papyrifera* in a provenance test plot planted in Wooster, Ohio, in 1986. 'Renci' was originated from the open pollinated cross in a birch selection/breeding program in Wooster, Ohio. The non-patented female parent was *Betula papyrifera* as well as the male parent. 'Renci' was first noticed with a pyramidal growth habit, white, essentially non-exfoliating bark and a very high resistance to the Bronze Birch Borer. The growth habit renders it ideal for clumping. The first act of asexual reproduction of 'Renci' was accomplished by the inventor from the initial selection in our test plot on New Carlisle, Ohio. Currently, asexual reproduction is accomplished by micropropagation or tissue culture in Olympia, Wash. Horticultural examination of selected units has demonstrated that the combination of characteristics as herein disclosed for 'Renci' are firmly fixed and retained through its successive generations of asexual reproduction. 'Renci' has been observed in Sturgeon Bay, Wis. and New Carlisle, Ohio and characteristics have been stably maintained. The cultivar reproduces true to type. The new cultivar has not been observed under all possible environmental conditions. The phenotype may vary somewhat with variations in environment such as temperature, day length and light intensity, without a change in the genotype of a cultivar. The following observation, measurements, and comparisons describe the plants grown in New Carlisle, Ohio, and Sturgeon Bay, Wis. under natural field conditions which approximate those generally used in commercial growing operations.

SUMMARY OF THE INVENTION

The following traits have been repeatedly observed and are determined to be basic characteristics of 'Renci' which in combination distinguish this birch tree as a new and distinct cultivar:

1. Distinctive pyramidal growth habit with branching angles about 38–40°.

2. Bark color changes as the tree matures; from brown turning to only slightly exfoliating white bark.
3. Very high resistance to the Bronze Birch Borer.
4. Rapid growth rate.

The new cultivar can be compared to nonpatented *Betula papyrifera*. The nonpatented plants have a loose oval growth habit and white exfoliating bark. They have variable resistance to the Bronze Birch Borer. The numbered traits above clearly distinguish the new cultivar from nonpatented *Betula papyrifera*.

BRIEF DESCRIPTION OF THE DRAWINGS

The accompanying color photographs show typical characteristics of 'Renci', with colors being as true as possible with illustration of this type.

DETAILED BOTANICAL DESCRIPTION

Figure 1:
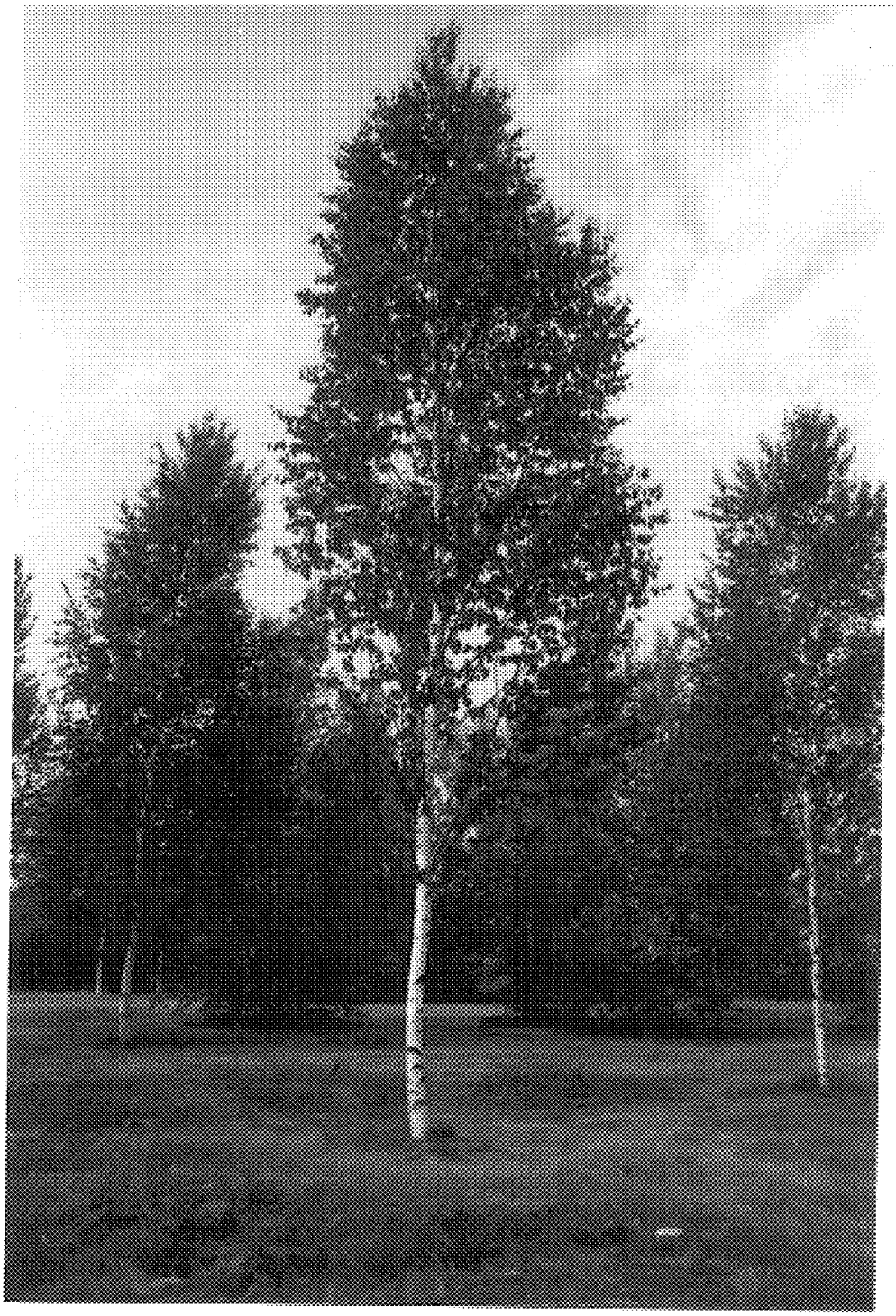
FIG. 1 is the side view of a specimen of 'Renci' showing the pyramidal growth habit.
Figure 2:
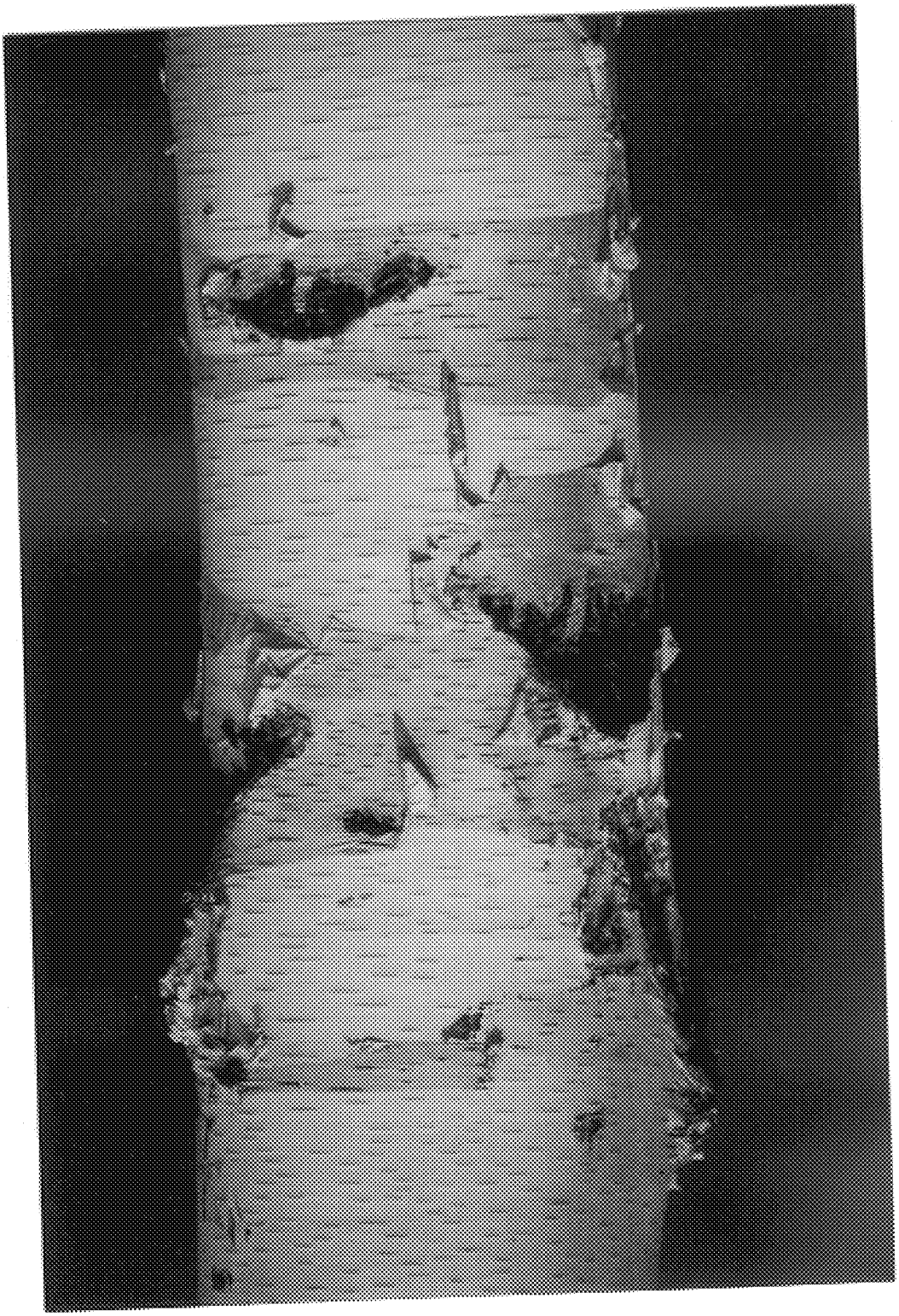
FIG. 2 shows the essentially non-exfoliating bark.
Figure 3:
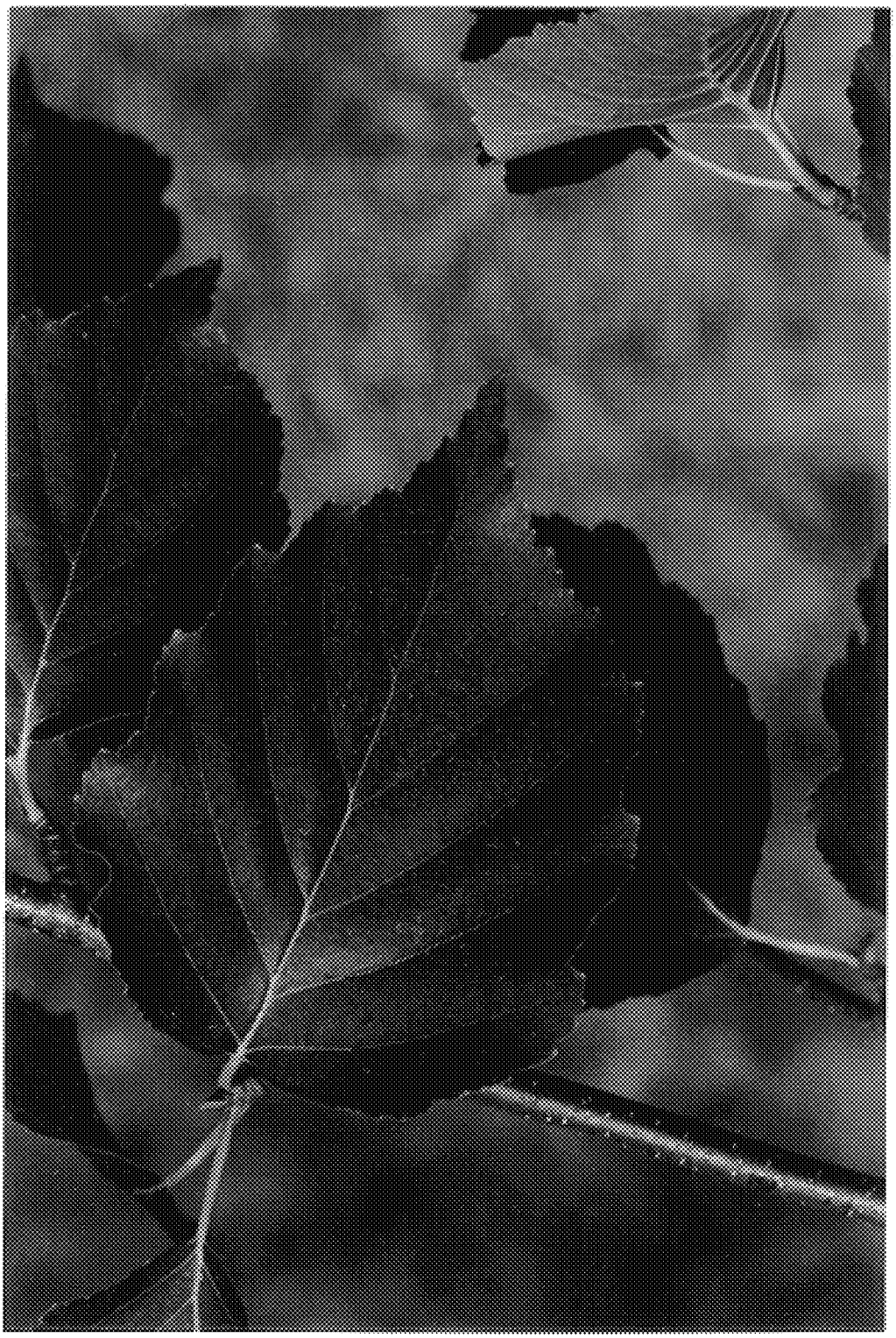
FIG. 3 shows a close-up of the upper side of a leaf.
Figure 4:
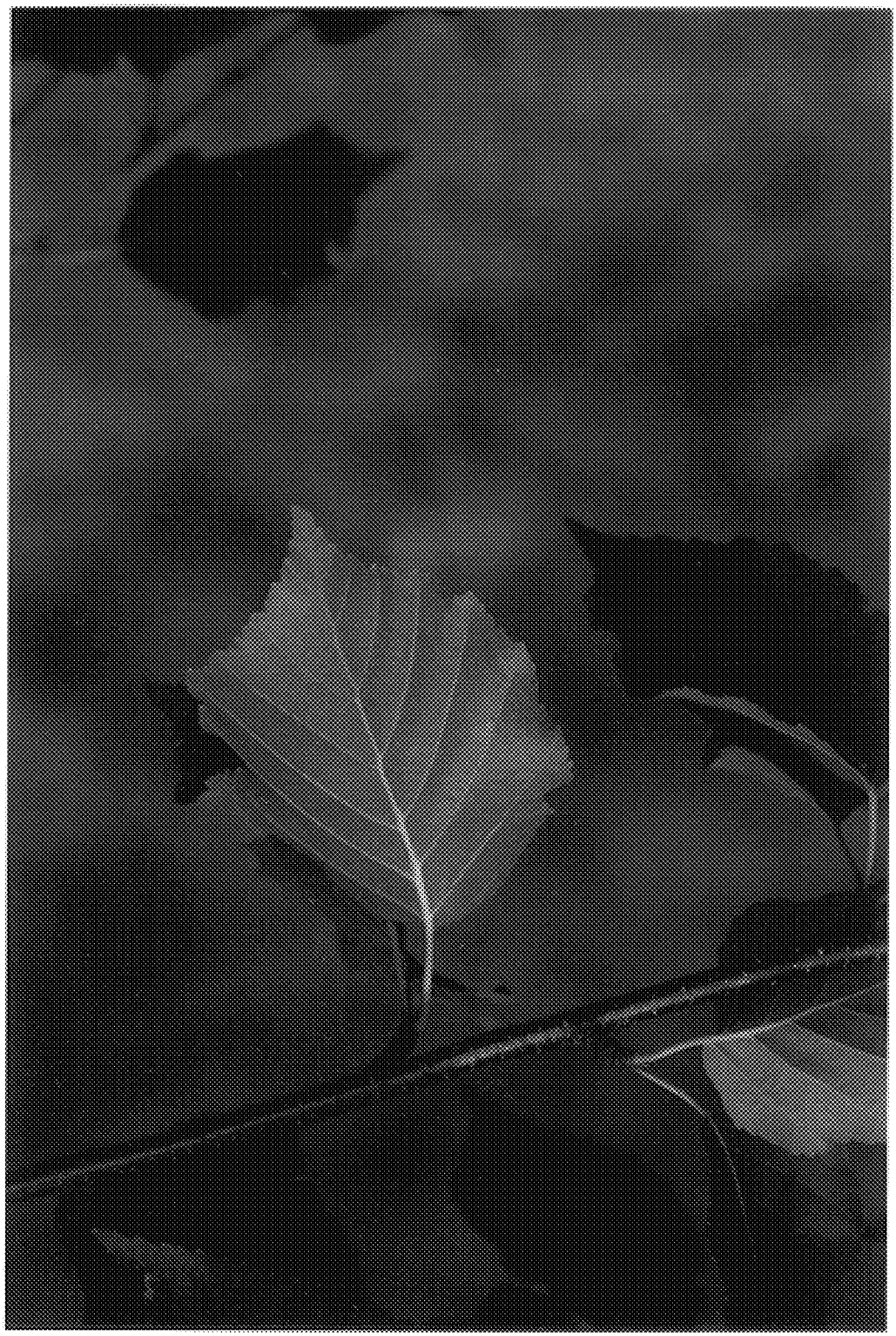
FIG. 4 shows a close-up of the under side of a leaf.

In the following description, color references are made to The Royal Horticultural Society (R.H.S.) Color Chart. The color values were determined in natural light in August 1999 in Sturgeon Bay, Wis.

Classification:

*Botanical.*—*Betula papyrifera* 'Renci'.

Parentage:

*Origin.*—The plant was selected from a test plot of *Betula papyrifera* in New Carlisle, Ohio.

*Parentage.*—Seed parent: *Betula papyrifera*. Pollen parent: *Betula papyrifera*.

Tree:

*Trunk.*—Single-trunked tree. Size: Diameter at age 13 is approximately 15 cm. At 1.2 m above the ground. The height is 13.3 m.

*Bark at maturity.*—White, fine textured only slight exfoliating close to (R.H.S. 155C).

*Branches.*—Angle of attachment: 38–40°. Spacing: Between whorls 30–50 cm. The branches are 3–4 cm in diameter measured at about 1.4 m when the tree is 2.4 meters high. Bark: Color changes with age: from brown RHS 200A to RHS 155D, at 4 years, brown RHS 200A turning to white close to RHS 155D with only slight exfoliation, fine texture. Lenticels: Small, but numerous, length 2–4 mm, width 1–2 mm. Color: RHS 166B.

*Height.*—13.3 m at about 13 years of age.

*Growth habit or form.*—Pyramidal, upright, when tree is 13.3 m high, it is about 5.5 m wide. Growth rate: rapid, about 0.8–2.0 m per year, depending on summer temperature, fertility and water availability.

*Foliage.*—Size of leaf: Length: with petiole 8–15 cm, without petiole 6–11 cm; Width: 4–8 cm; Leaf arrangement: alternate; Shape of leaf: serrate, rounded base, ovate with acute apex acuminate apices and double serrate margins; Texture: Smooth; Ribs and veins: mid-rib with 18 veins (RHS 145B) sub opposite. Pubescence distribution: on under side of mid rib and in axils of veins; Quantity: Singles or spurs of two or more, usually two leaves, approximately 20 leaves/50 cm of stem. Color: upper side, dark green (RHS 147A), under side dark green (RHS 147B). Petiole: Length: 2–4 cm. Diameter: 2 mm: Color: (RHS 145). No stipules.

*Disease and pest resistance.*—Very high resistance to Bronze Birch Borer as compared with about 240 other trees in New Carlisle, Ohio. High resistant to Leafhoppers.

*Disease and pest susceptibility.*—Moderately susceptible to leafminor.

*Winter hardiness/drought/heat resistance.*—Winter hardiness in Zone 3 and good drought/heat resistance in Zone 7.

*Flowers.*—None have been observed to date.

*Reproductive organs.*—Typical of the species.

*Comparison with other plants.*—Comparison of this cultivar with 'Oenci' is as follows:

DIFFERENCES

| | 'Renci' | 'Oenci' |
|---|---|---|
| Shape | Pyramidal | Broad dense pyramid |
| Bark | White-essentially Non-effaliality | White - exfoliating |
| Branches Color | RHS 200A | RHS 166A |
| Leaf Color | RHS 147A | RHS 137A |
| Draught tolerance | Good | Excellent |

What is claimed is:

1. A new and distinct cultivar of birch tree named 'Renci', as illustrated and described.

* * * * *